US00PP28532P2

(12) United States Plant Patent
Koekkoek

(10) Patent No.: US PP28,532 P2
(45) Date of Patent: Oct. 17, 2017

(54) CARNATION PLANT NAMED 'HILODEAMY'

(50) Latin Name: ***Dianthus* L.**
Varietal Denomination: Hilodeamy

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 14/999,644

(22) Filed: Jun. 8, 2016

(51) Int. Cl.
*A01H 5/02* (2006.01)

(52) U.S. Cl.
USPC ..... Plt./272

(58) Field of Classification Search
USPC ..... Plt./272
See application file for complete search history.

*Primary Examiner* — Annette Para
(74) *Attorney, Agent, or Firm* — C. A. Whealy

(57) ABSTRACT

A new and distinct cultivar of Carnation plant named 'Hilodeamy', characterized by its compact, uniformly mounding and upright to broadly spreading plant habit; relatively small leaves; freely flowering habit; white and red purple bi-colored semi-double flowers; and good container performance.

1 Drawing Sheet

Botanical designation: *Dianthus* L.
Cultivar denomination: 'HILODEAMY'.

BACKGROUND OF THE INVENTION

The present invention relates to a new and distinct cultivar of Carnation plant, botanically known as *Dianthus* L., grown commercially as a container plant and hereinafter referred to by the name 'Hilodeamy'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in June, 2011 of *Dianthus* L. 'Kermit', not patented, as the female, or seed, parent with a proprietary selection of *Dianthus* L. identified as code number A56048-01, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal cuttings propagated in a controlled greenhouse environment in De Kwakel, The Netherlands since October, 2012 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilodeamy'. These characteristics in combination distinguish 'Hilodeamy' as a new and distinct Carnation plant:

1. Compact, uniformly mounding and upright to broadly spreading plant habit.
2. Relatively small leaves.
3. Freely flowering habit.
4. White and red purple bi-colored semi-double flowers.
5. Good container performance.

Plants of the new Carnation differ primarily from plants of the female parent, 'Kermit', in the following characteristics:

1. Plants of the new Carnation have shorter branches than plants of 'Kermit'.
2. Plants of the new Carnation are more freely branching than plants of 'Kermit'.
3. Plants of the new Carnation and 'Kermit' differ in flower color as plants of 'Kermit' have yellow green-colored flowers.

Plants of the new Carnation differ primarily from plants of the male parent selection in the following characteristics:

1. Plants of the new Carnation have smaller flowers than plants of the male parent selection.
2. Flowers of plants of the new Carnation have fewer petals than flowers of plants of the male parent selection.

Plants of the new Carnation also can be compared to plants of *Dianthus caryophyllus* 'Hilprot', disclosed in U.S. Plant Pat. No. 27,175. In side-by-side comparisons, plants of the new Carnation differ primarily from plants of 'Hilprot' in the following characteristics:

1. Plants of the new Carnation have slightly longer branches than plants of 'Hilprot'.
2. Plants of the new Carnation have larger flowers than plants of 'Hilprot'.
3. Plants of the new Carnation and 'Hilprot' differ in flower color as plants of 'Hilprot' have purple-colored flowers with narrow light pink-colored margins.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilodeamy' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 17° C., night temperatures averaged 12° C. and light levels averaged 7,000 lux. Plants used for the photograph and description were twelve weeks old. In the following description, color references are made to The Royal Horticultural Society Colour Chart, 2015 Edition, except where general terms of ordinary dictionary significance are used.

Botanical classification: *Dianthus* L. 'Hilodeamy'.

Parentage:

*Female, or seed, parent.*—*Dianthus* L. 'Kermit', not patented.

*Male, or pollen, parent.*—Proprietary selection of *Dianthus* L. identified as code number A56048-01, not patented.

Propagation:

*Type.*—By terminal cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; whitish in color.

*Rooting habit.*—Moderate branching; medium density.

Plant description:

*Plant and growth habit.*—Herbaceous perennial, typically grown as a container plant; compact, uniformly mounding, upright to broadly spreading plant habit; moderately vigorous growth habit.

*Plant height, soil level to top of foliar plane.*—About 18.4 cm.

*Plant height, soil level to top of floral plane.*—About 21 cm.

*Plant diameter or spread.*—About 27.3 cm.

*Lateral branches.*—Branching habit: Freely branching habit with about eight main (basal) stems; each main stem with about eight lateral branches; pinching enhances lateral branch development. Length: About 13.3 cm. Diameter: About 3 mm. Internode length: About 2.5 cm. Strength: Strong. Aspect: Upright to about 50° from vertical. Texture and luster: Smooth, glabrous, waxy cuticle; matte. Color, developing: Close to 144C; at internodes, close to 145C. Color, developed: Close to NN137B; thin waxy cuticle, close to 188B.

Leaf description:

*Arrangement.*—Opposite, simple; sessile.

*Length.*—About 9.6 cm.

*Width.*—About 5.5 mm.

*Shape.*—Narrowly oblanceolate; moderately carinate.

*Apex.*—Acute.

*Base.*—Attenuate; decurrent.

*Margin.*—Entire.

*Texture and luster, upper and lower surfaces.*—Smooth, glabrous, waxy cuticle; matte.

*Venation pattern.*—Parallel.

*Color.*—Developing leaves, upper surface: Close to 143C; towards the base, close to 144C. Developing leaves, lower surface: Close to 143B to 143C; towards the base, close to 144B to 144C. Fully expanded leaves, upper surface: Close to NN137C; venation, close to NN137C. Fully expanded leaves, lower surface: Close to NN137B; thin waxy cuticle, close to 189A; venation, close to 143A and 143B.

Flower description:

*Flower form and flowering habit.*—Semi-double flowers arranged singly or in pairs; freely flowering habit with about 130 flowers developing during the flowering season; flowers face mostly upright to slightly outwardly.

*Natural flowering season.*—Flowering is continuous from the spring to late summer in The Netherlands; plants begin flowering about nine to eleven weeks after planting.

*Postproduction longevity.*—Flowers last about ten days on the plant; flowers not persistent.

*Fragrance.*—Moderately fragrant; clove-like, sweet.

*Flower buds.*—Length: About 3.3 cm. Diameter: About 1 cm. Shape: Oblanceolate. Texture and luster: Smooth, glabrous; matte. Color: Close to 137B; towards the base, close to 144C; sepal apices tinged with close to N200A; petal apices, close to 75D.

*Flower diameter.*—About 4.6 cm.

*Flower depth.*—About 4.6 cm.

*Petals.*—Quantity and arrangement: About five petals arranged in a single whorl. Length: About 4.9 cm. Width: About 2.6 cm. Shape: Spatulate. Apex: Praemorse; slightly crinkled. Base: Narrowly cuneate. Margin: Towards the apex, irregularly dentate; towards the base, entire; slightly undulate. Texture and luster, upper and lower surfaces: Smooth, glabrous; slightly velvety; matte. Color: When opening, upper surface: Towards the margins and apex, close to NN155D; center, close to slightly darker than 60A with a radial band, close to 187A; towards the base, close to 73B to 73C; at the base, close to 145C. When opening, lower surface: Towards the margins and apex, close to NN155D; center, close to 59D; at the base, close to 145C. Fully opened, upper surface: Towards the margins and apex, close to NN155B to NN155C; central blotch, close to 59C and 60B with a radial band, close to 184B; towards the base, close to 73A; at the base, close to 145C; venation, similar to lamina colors; colors do not change with development. Fully opened, lower surface: Towards the margins and apex, close to NN155C to NN155D; radial band, close to 184D; towards the base, close to 73A; at the base, close to 145C; venation, close to 184D; colors do not change with development.

*Petaloids*.—Quantity and arrangement: About ten petaloids arranged in about two whorls. Length: About 3.9 cm. Width: About 1.5 cm. Shape: Irregularly spatulate. Apex: Praemorse; slightly crinkled. Base: Narrowly cuneate. Margin: Towards the apex, irregularly dentate; towards the base, entire; moderately undulate. Texture and luster, upper and lower surfaces: Smooth, glabrous; slightly velvety; matte. Color: When opening, upper surface: Towards the margins and apex, close to NN155D; center, close to slightly darker than 60A with a radial band, close to 187A; towards the base, close to 73B to 73C; at the base, close to 145C. When opening, lower surface: Towards the margins and apex, close to NN155D; center, close to 59D; at the base, close to 145C. Fully opened, upper surface: Towards the margins and apex, close to NN155B to NN155C; central blotch, close to 59C and 60B with a radial band, close to 184B; towards the base, close to 73A; at the base, close to 145C; venation, similar to lamina colors; colors do not change with development. Fully opened, lower surface: Towards the margins and apex, close to NN155C to NN155D; radial band, close to 184D; towards the base, close to 73A; at the base, close to 145C; venation, close to 184D; colors do not change with development.

*Sepals*.—Quantity and arrangement: Five sepals arranged in a single whorl; proximal 75% portion of the sepals are fused into a campanulate-shaped calyx. Calyx length: About 2.5 cm. Calyx diameter: About 1.1 cm. Sepal length: About 2.5 cm. Sepal width, at base of "free" portion: About 6 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 147D; towards the apex, close to 147C. When opening, lower surface: Close to 137B; towards the base, close to 144C; apex, tinged with close to N200A. Fully opened, upper surface: Close to 147D; towards the apex, close to 147C. Fully opened, lower surface: Close to 147A; towards the base, close to 144B to 144C.

*Peduncles*.—Length: About 1.5 cm. Diameter: About 1.5 mm. Strength: Moderately strong. Aspect: About 20° from the stem axis. Texture and luster: Smooth, glabrous, waxy; moderately glossy. Color: Close to NN137B; thin waxy layer, close to 188B.

*Reproductive organs*.—Stamens: Quantity: About two stamens per flower; strongly deformed. Filament length: About 2.1 cm. Filament color: Close to 157D. Anther length: About 1 mm. Anther shape: Oblong. Anther color: Close to N77B. Pollen: None produced. Pistils: Quantity: About two per flower. Pistil length: About 2.2 cm. Stigma diameter: About 4 mm. Stigma shape: Pointed, spirally curved. Stigma color: Close to NN155D. Style length: About 1.9 cm. Style color: Close to NN155D. Ovary color: Close to N144A; towards the base, close to 157C. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be suitable for USDA Hardiness Zones 5 to 9.

It is claimed:

1. A new and distinct Carnation plant named 'Hilodeamy' as illustrated and described.

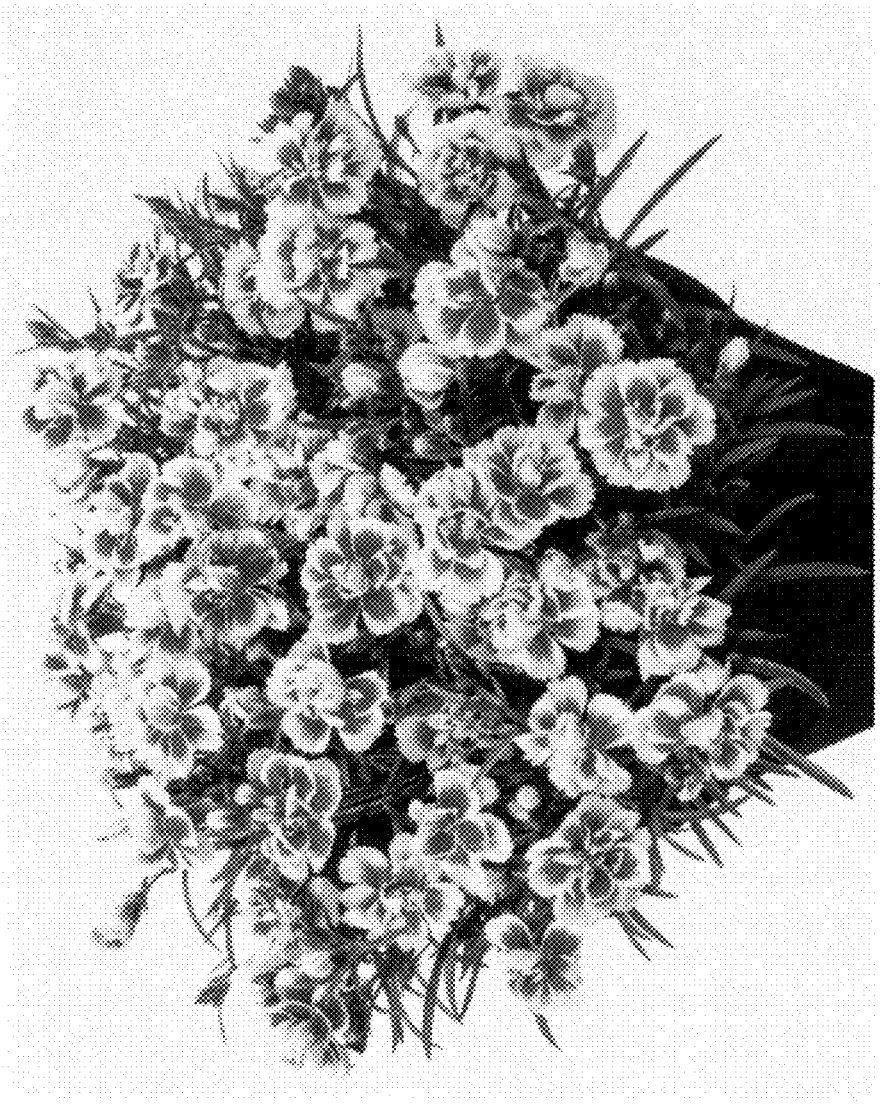

* * * * *